United States Patent
Wang et al.

(10) Patent No.: US 6,911,916 B1
(45) Date of Patent: Jun. 28, 2005

(54) METHOD AND APPARATUS FOR ACCESSING MEDICAL DATA OVER A NETWORK

(75) Inventors: Gang Wang, Santa Barbara, CA (US); Joseph F. Hahn, Orange Village, OH (US); Amante Mangaser, Goleta, CA (US); David B. Roe, Santa Barbara, CA (US); Charles P. Steiner, Cleveland, OH (US); Darrin R. Uecker, Santa Barbara, CA (US)

(73) Assignees: The Cleveland Clinic Foundation, Cleveland, OH (US); Intuitive Surgical, Inc., Sunnyvale, CA (US)

( * ) Notice: Subject to any disclaimer, the term of this patent is extended or adjusted under 35 U.S.C. 154(b) by 232 days.

(21) Appl. No.: 09/615,641

(22) Filed: Jul. 13, 2000

Related U.S. Application Data (63) Continuation-in-part of application No. 09/354,944, filed on Jul. 15, 1999, which is a continuation-in-part of application No. 08/693,352, filed on Aug. 6, 1996, which is a continuation-in-part of application No. 08/669,629, filed on Jun. 24, 1996, now abandoned.

(51) Int. Cl.[7] .......................... G05B 23/02; A61B 5/00; G10L 21/00
(52) U.S. Cl. ...................... 340/825; 340/3.5; 600/300; 704/275
(58) Field of Search ...................... 340/3.1, 3.3, 3.32, 340/3.5; 600/300; 704/275; 361/197, 198, 199

(56) References Cited

U.S. PATENT DOCUMENTS

| | | | |
|---|---|---|---|
| 4,158,750 A | 6/1979 | Sakoe et al. | |
| 4,207,959 A | 6/1980 | Youdin et al. | |
| 4,216,462 A * | 8/1980 | McGrath et al. | ............ 600/301 |
| 4,641,292 A | 2/1987 | Tunnell et al. | |
| 4,776,016 A | 10/1988 | Hansen | |
| 4,807,273 A | 2/1989 | Haendle | |
| 4,989,253 A | 1/1991 | Liang et al. | |
| 5,230,023 A | 7/1993 | Nakano | |
| 5,274,862 A | 1/1994 | Palmer, Jr. et al. | |
| 5,303,148 A * | 4/1994 | Mattson et al. | ............. 600/437 |
| 5,335,313 A | 8/1994 | Douglas | |
| 5,345,538 A | 9/1994 | Narayannan et al. | |
| 5,372,147 A | 12/1994 | Lathrop, Jr. et al. | |
| 5,500,854 A * | 3/1996 | Uotila | ........................ 370/254 |
| 5,511,256 A | 4/1996 | Capaldi | |
| 5,566,272 A | 10/1996 | Brems et al. | |
| 5,572,999 A | 11/1996 | Funda et al. | |
| 5,609,560 A * | 3/1997 | Ichikawa et al. | ............ 600/101 |
| 5,627,584 A * | 5/1997 | Nishikori et al. | ............. 348/72 |
| 5,640,953 A * | 6/1997 | Bishop et al. | .............. 600/300 |
| 5,713,350 A * | 2/1998 | Yokota et al. | .............. 600/300 |

(Continued)

FOREIGN PATENT DOCUMENTS

| | | |
|---|---|---|
| WO | WO 96/09587 | 3/1996 |
| WO | WO 99/21165 | 4/1999 |

*Primary Examiner*—Brian Zimmerman
*Assistant Examiner*—Tara Young
(74) *Attorney, Agent, or Firm*—Fish & Richardson P.C.

(57) ABSTRACT

A method and apparatus for retrieving, accessing, and storing medical data relating to a patient during a medical procedure. The invention provides a single interface to many disparate forms of medical data, which is accessible over a local area network, wide area network, direct connection, or combinations thereof. In one embodiment, an operating room control system for use during a medical procedure on a patient includes an input device, a display device, and a controller that is coupled to the input device and the display device. The controller receives one or more user inputs, transmits a command to a server located outside of the operating room to retrieve medical data, receives the medical data from the server, and displays the medical data on the display device.

24 Claims, 8 Drawing Sheets

U.S. PATENT DOCUMENTS

| | | |
|---|---|---|
| 5,715,548 A | 2/1998 | Weismiller et al. |
| 5,729,659 A | 3/1998 | Potter |
| 5,771,511 A | 6/1998 | Kummer et al. |
| 5,788,688 A | 8/1998 | Bauer et al. |
| 5,809,591 A | 9/1998 | Capaldi et al. |
| 5,812,978 A | 9/1998 | Nolan |
| 5,841,950 A | 11/1998 | Wang et al. |
| 5,842,173 A * | 11/1998 | Strum et al. .................... 705/1 |
| 5,857,967 A * | 1/1999 | Frid et al. .................... 600/301 |
| 5,884,350 A | 3/1999 | Kurze |
| 5,970,457 A | 10/1999 | Brant et al. |
| 6,224,542 B1 | 5/2001 | Chang et al. |
| 6,278,975 B1 | 8/2001 | Brant et al. |

* cited by examiner

METHOD AND APPARATUS FOR ACCESSING MEDICAL DATA OVER A NETWORK

REFERENCE TO RELATED APPLICATIONS

The presently filed application is a continuation-in-part application of a U.S. Patent Application entitled "GENERAL PURPOSE DISTRIBUTED OPERATING ROOM CONTROL SYSTEM", which is assigned application Ser. No. 09/354,944, filed Jul. 15, 1999, and is currently pending, which is a continuation-in-part application of a U.S. Patent Application entitled "GENERAL PURPOSE DISTRIBUTED OPERATING ROOM CONTROL SYSTEM", assigned application Ser. No. 08/693,352, and filed Aug. 6, 1996, now pending, which is a continuation-in-part application of a U.S. Patent Application entitled "MULTI-FUNCTIONAL SURGICAL CONTROL SYSTEM AND SWITCHING INTERFACE", assigned application Ser. No. 08/669,629, filed Jun. 24, 1996, now abandoned.

BACKGROUND OF THE INVENTION

1. Field of the Invention

The present invention relates generally to control systems, and specifically, to information control systems for accessing and integrating medical data for medical purposes.

2. Description of the Related Art

Many surgical procedures are performed with multiple instruments. For example, some laproscopic procedures are performed utilizing a robotic arm system produced by Computer Motion, Inc. of Goleta, Calif. to hold and move an endoscope. The surgeon may also use a laser to cut tissue, an electrocautery device to cauterize the tissue, and lights to illuminate the surgical site.

Often, it is necessary for a surgeon or doctor to read and study patient information before performing a surgical procedure or examination. The patient information may include patient's medical history, reactions to medication, viewing X-rays and other images and video, etc. This requires the surgeon to review files of the patient, which may located in disparate places, study the files, and copy documents to take to the operating room. The doctor may also have to memorize the patient information since access to such information in a sterile environment is difficult. Alternatively, the doctor can utilize a nurse to look up the information during the surgery, medical procedure, etc. It is imperative that the information obtained regarding the patient is accurate in order to make correct decisions quickly and efficiently.

BRIEF SUMMARY OF THE INVENTION

The present invention comprises a method and apparatus for accessing and/or capturing medical data during a medical procedure. In one embodiment, an operating room control system for use during a medical procedure on a patient includes an input device, a display device, and a controller that is coupled to the input device and the display device. The controller receives one or more user inputs, in response to a user input, transmits a command to a server located outside of the operating room to retrieve patient information, receives the patient information from the server, and displays the patient information on the display device.

Other embodiments are described and claimed herein.

DETAILED DESCRIPTION

Figure 1:
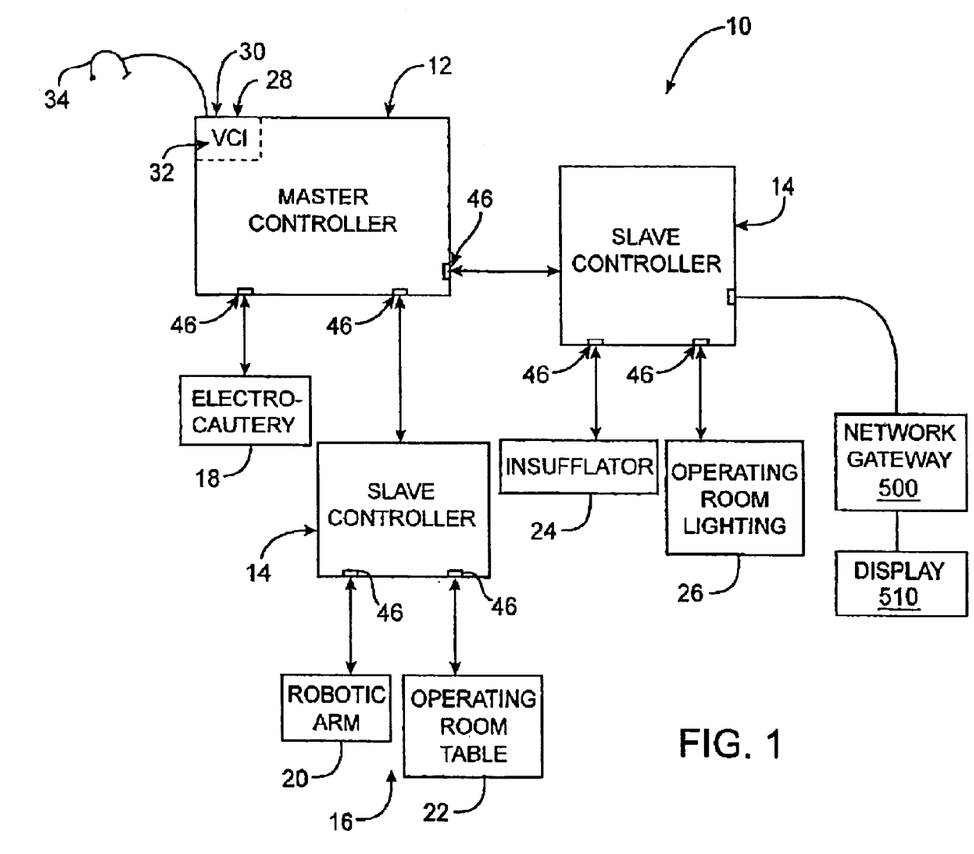
FIG. 1 is a block diagram of a master controller in electrical communication with both slave controllers and operating room devices, according to one embodiment of the present invention.

Referring now to the drawings, there is shown in FIG. 1 an operating room control system shown generally at 10. The operating room control system, or control system 10, generally comprises a master controller 12, which is preferably attached to at least one slave controller 14. Although the exemplary preferred embodiment is shown as having both a master controller 12 and at least one slave controller 14 in electrical communication therewith, the control system 10 may be implemented with only a master controller 12 as will be described hereinbelow.

The master controller 12 is electrically connected to and in electrical communication with a plurality of devices 16 via a plurality of communication ports 46. Alternatively, the master controller 12 may be connected to any slave or specific medical device via wireless communications systems such as IR or RF signal transmitters and receivers on each of the master 12, slaves 14, and devices 16. Some of these devices 16 may be at least one slave controller 14 the operation of which will be described hereinbelow. Other devices that are intended to be electrically connected to the master controller 12, either directly or via the at least one slave controller 14 include devices that are commonly found in an operating room environment.

For purposes of non-limiting example, directly connected to the master controller 12 in FIG. 1 is an electrocautery device 18. A robotic arm 20 for holding and manipulating an endoscope, such as that produced by Computer Motion of Goleta, Calif. and marketed under the tradename AESOP is electrically connected with the master controller 12 via one of the at least one slave controllers 14. Also in electrical communication with the master controller 12 via a slave controller is an operating room table 22, an insufflator 24, and an operating room lighting system 26. It is envisioned that any electrically controlled device utilized in an operating room environment may be attached to the master controller 12 either directly or via one of the at least one slave controllers 14.

The master controller 12 is configured to provide a main user interface for each of the devices electrically connected thereto. As such, a doctor can manipulate the operating room environment in a simpler and more direct fashion. Currently, each device in an operating room includes a separate interface. The proximity of the doctor to each interface requires a substantial amount of movement either on the part of the doctor or a nurse to effectuate changes required by the doctor during a medical procedure.

For example, if the doctor needs the lights dimmed slightly, then a nurse currently has to approach the lighting system of the operating room and dim the lights. It would be highly advantageous for the doctor to be able to control such changes directly to keep movement in the operating room to a minimum to increase sterility, and because direct control by the doctor of the operating room environment and the devices he or she is using ensures the highest degree of safety with the smallest amount of error due to miscommunication between people in the operating room. Minimization of movement in an operating room environment is additionally advantageous to reduce the risk of contamination of specific sterile instruments, as well as the operative site itself.

To effectuate such a control system 10, the master controller 12 generally comprises a voice control interface (VCI) 32. The VCI 32 includes means 28 for receiving selection commands from a user wherein each selection command is associated with one specific device in electrical communication with the master controller 12. This is accomplished by providing the master controller 12 a list of the devices that are in electrical communication therewith upon start-up of the control system 10. The process and hardware for providing the master controller 12 with such a list will be described hereinbelow.

Figure 2:
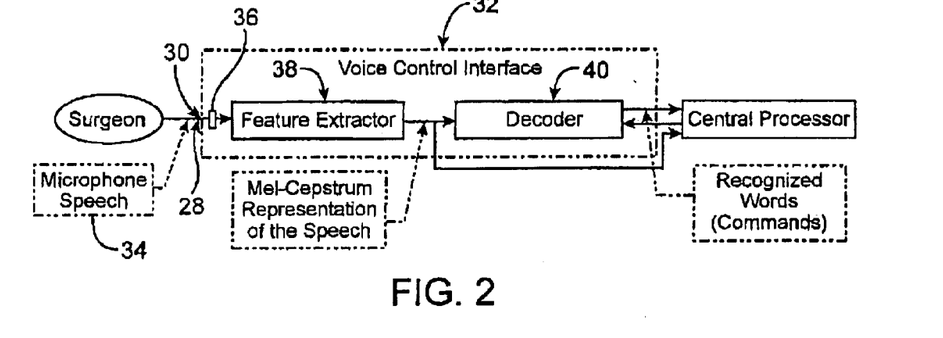
FIG. 2 is an exemplary block diagram of the voice control interface.

As shown in FIG. 2, The VCI 32 additionally comprises means 30 for receiving control commands from a user. In the preferred embodiment, both the means 28 for receiving selection commands and the means 30 for receiving control commands may coexist in the VCI 32 as a microphone 34, for receiving the actual speech of the user, an analog to digital converter 36 for converting the analog speech into a digital representation thereof, a feature extractor 38 for converting the digital representation to a digital representation that is suited for decoding, and a decoder 40 for comparing the features of the transformed digital representation of the speech to a set of pre-saved user-models 41 to determine whether the speech received at the microphone 34 was a selection command, a control command, or some other speech to be ignored by the master controller 12. Such "other speech" would include extraneous noise, speech between the doctor and another person in the operating suite, as well as speech of other people in the operating suite in general.

Feature extractors, such as the one employed in the present invention, are well known in the art of voice recognition. Feature vectors are preferably generated by the feature extractor 38 utilizing techniques such as Mel-Cepstrum, or linear prediction. It is to be appreciated that such techniques are well-known and are employed in the feature extractor 38 to develop feature vectors that represent speech received by the VCI 32.

Additionally, voice software is also available that provides extractors and decoders such as the ones set out in the present application. As such, although a specific implementation is presented herein for voice recognition, it may be carried out by the inclusion of a pre-made voice recognition system that is purchased from a vendor such as Creative labs under the tradename VOICE BLASTER, Dragon Dictate produced by Dragon Systems, or VOICE PAD produced by Kurzweil AI of Massachusetts, each of these companies produce front-end voice recognition systems.

The decoder 40 utilizes the information produced by the feature extractor 38, by matching the stored user models 41 to the output of the feature extractor 38 utilizing a well-known method, such as a Hidden Markov Modeling. One Hidden Markov Model (HMM) is created for each phoneme. The HMMs are trained to identify their respective phonemes given the Mel-Cepstrum output from the feature extractor 38. The use of Hidden Markov Models for voice recognition is generally well known.

Figure 3:
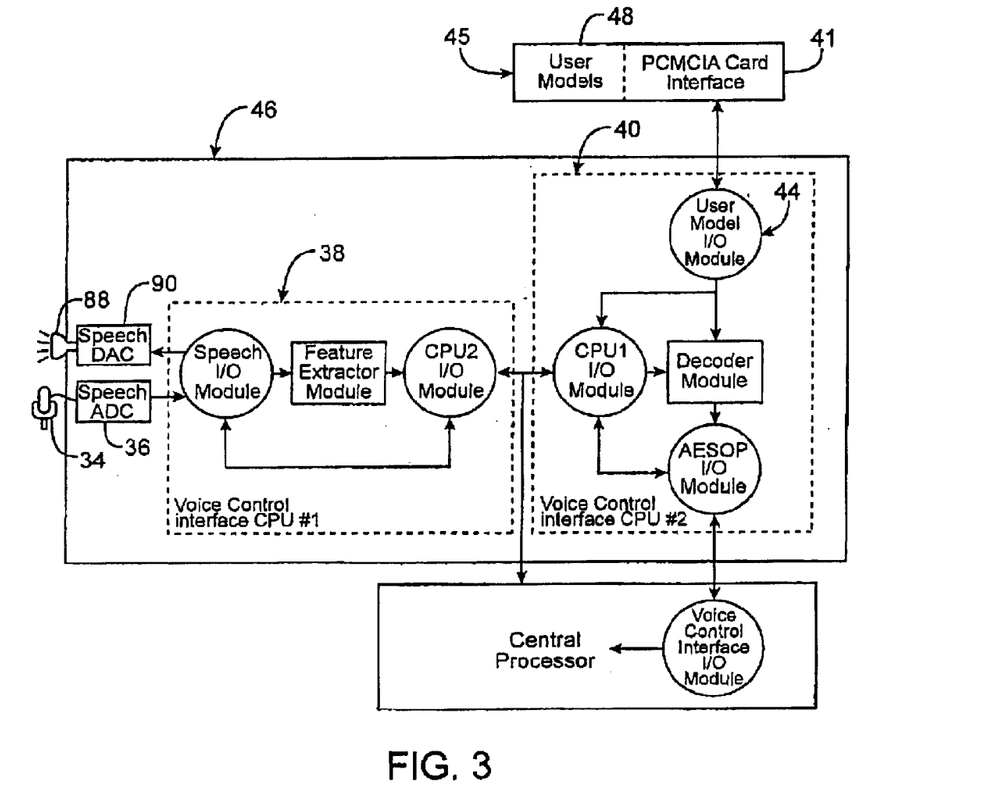
FIG. 3 is an exemplary schematic of the voice control interface card.

The stored user models 41 used by the decoder 40 may be placed in a memory 44 associated with the VCI itself. As depicted in FIG. 3, such a memory 44 may be incorporated onto a VCI board 46 as an EPROM, a PROM or some other programmable memory storage device. However, it is preferable to store the models on a transportable memory device 45, such as a disk, transportable storage medium or the like. It is even more preferable that the transportable memory device be a PCMCIA format card 48 as data transfer times are reduced and the ruggedness of the system is increased. PCMCIA format cards retain data better than floppy disks. Additionally, the configuration of currently produced PCMCIA cards allows for additional program data to be stored on the PCMCIA format card and downloaded into the master controller 12 when system changes are made (i.e. upgrades to the system software etc.). Therefore, the use of such a PCMCIA form factor card is preferable in the control system 10 of the present invention.

FIG. 3 depicts, in more detail, the VCI 32. Once the user's speech has been digitized at the A/D converter 36, it is fed to the feature extractor 38. The feature extractor 38 functions as set out hereinabove. In more detail, the feature extractor 38 converts the digitized signal into a representation that is suitable for decoding (e.g. Mel-Cepstrum). This representation is then passed to the decoder 40 which compares the representations produced at the feature extractor 38 to the models stored on a memory 44 which contains the user models 41. The memory 44 may be supplied the models 41 via a downloading process from the transportable memory device 45. The models stored in the memory 44 constitute a lexicon, which is the entire set of valid pronunciations, or all of the valid words that the master 12 is to recognize. Because the lexicon is stored on a transportable data storage medium 41, the lexicon may be added to or subtracted from depending upon the devices that are to be connected to the master controller 12. In this fashion, if new equipment is purchased at a date subsequent to the purchase of the master controller 12, then new words may be added to the lexicon through a well-known data acquisition technique, wherein the user speaks the words that are to be added to the lexicon and they are used to update the user models 41 on the transportable memory 45.

In one or more implementations of the present system 10, there is provided one master controller 12 and at least one slave 14 controller. In such a configuration, which will be discussed in more detail hereinbelow, once the master controller or master 12 receives a selection command, all speech received at the VCI 32 of the master 12 that is not a new selection command is fed to the feature extractor of the appropriately attached slave 14. In this way, a plurality of devices may be attached to several different controllers and the lexicon stored in each controller does not have to be downloaded into the master 12. The master 12 only contains the lexicon of all the devices that may be connected to the system 10 as well as the lexicon for the commands of those devices that are directly attached to the master 12 as opposed to being attached to a slave 14 which is, in turn, attached to the master 12.

All the other controllers, which for purposes herein, are referred to as slaves 14, include the lexicon for the devices that are directly connected thereto. For example, in FIG. 1, one slave includes the lexicon for the control commands and the select commands for a robotic arm and an operating table. This way, that controller can have a microphone plugged into the VCI which is included in the unit and it may serve as a solo unit. Or, depending upon the configuration of the control system 10, it may actually server as a master. The entire system 10 is configurable at startup and as such is expandable. Every controller preferably includes a VCI.

The decoder 40 additionally contains a language model. This term is well-known on the art and will be explained further hereinbelow. In essence, certain words may be validly said in certain orders. The language model is implemented by developing a network representing all the valid possibilities of word combinations and decoding the extracted vectors along each path in the network. Whichever path has the highest probability of matching the incoming speech, the information associated with that path is selected by the decoder 40. It is to additionally be appreciated that to carry out the present invention, a silence path is available and an unrecognized command path is provided as well. As such, even though a user speaks, if valid commands are not given, the system 10 will not respond.

Figure 5:
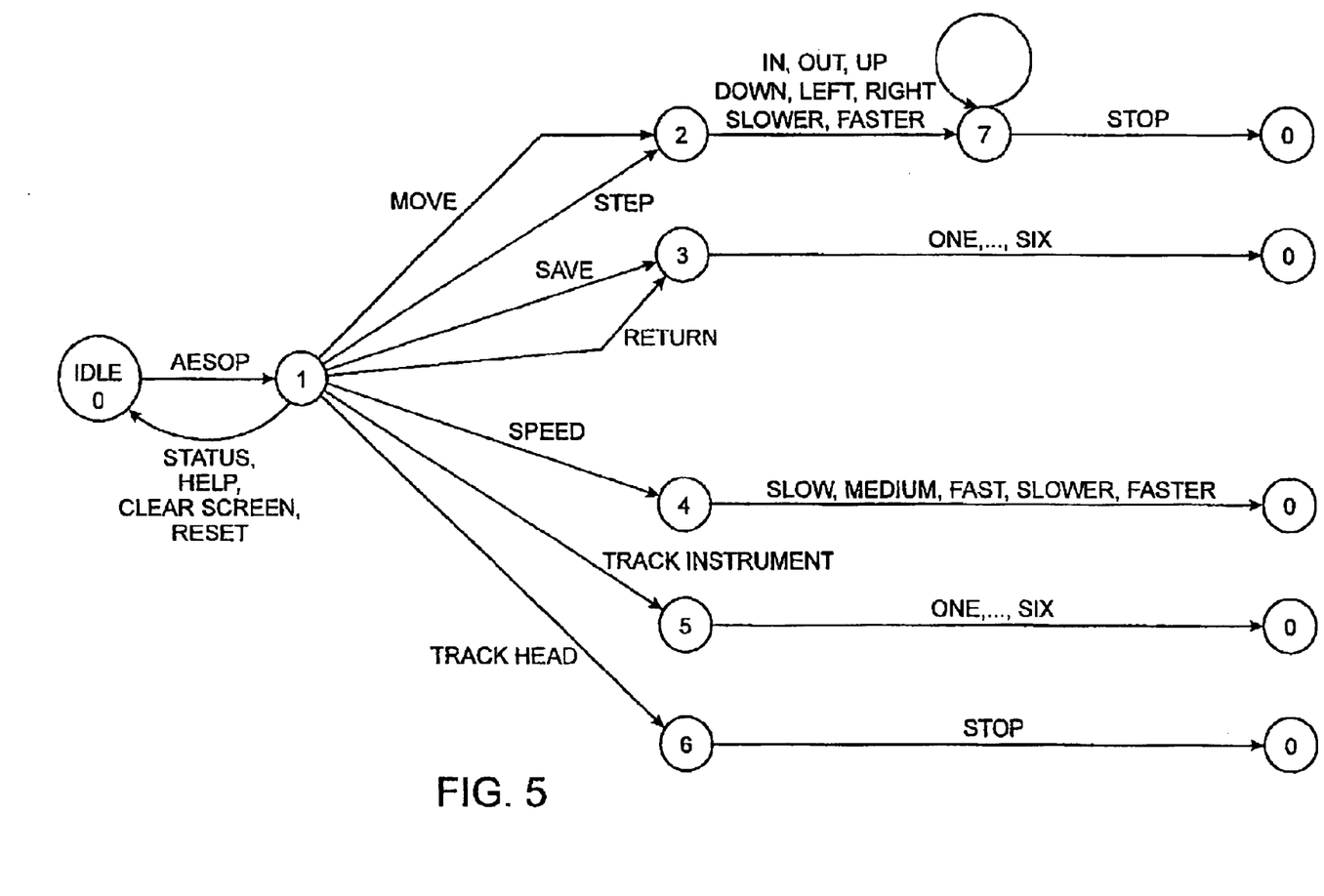
FIG. 5 is an exemplary tree diagram of a grammar for operating a device.

FIG. 5 sets out one exemplary language model for the proper operation of the robotic arm 20. Such language models are developed for each device in electrical communication with the master controller 12. Once again, a device may be in wireless communication with the master controller 12. It is preferable to store the language models for each device in their respective controller. For example, if a device is directly connected to a slave 14 then the control language model (that language model containing the language used to control the device) for the device is stored in the slave VCI. If the device is directly connected to the master 12 then the control language model is included in the VCI of the master 12. It is to be appreciated that the select language model must be stored in the master 12 for all the possible devices that may be directly connected to the master 12 as opposed to being connected to a slave. As such, depending upon what devices are connected to the system at any given time, a user may select from any of the connected devices. If a device is not connected, the system will recognize this upon startup and will not attempt to access the device as it is not there. This will be discussed in more detail hereinbelow.

If a device is connected directly to the master controller 12, then it is preferable to store the language model for controlling the device either in the VCI itself, or in the transportable memory 45. The advantages of this configuration are set out hereinbelow with respect to the startup of the control system 10.

If a select command is given for a device that is directly connected to the master 12, then the information is passed to the decoder in the master 12 and the decoder 40 generates a packet 52 of information. The packet includes the address of the device to be operated, a code representing the specific operation, and a checksum to ensure that as the packet 52 is transferred over various busses, the data does not become corrupted. Such information packaging is well-known although the specific package set out hereinabove has heretofore not been utilized to control one of a plurality of medical devices. Data checking using a checksum is also well-known in the art.

The decoder 40, upon decoding a valid selection command, activates the address of the device which has been stored in a lookup table and is related to the device. This is accomplished as follows. At startup every controller, whether the master 12 or a slave 14 knows the addresses of its communication ports. It sends a query to each communication port to see if a device is connected thereto. If so, an adapter connected to the device specifies the name of the device and an indication that it is functioning properly. Such adapters are well known in the electrical arts and as such will not be further discussed herein. Every slave controller establishes a lookup table of addresses and associated device codes or names. The device codes or names are transmitted to the master 12 which includes all the devices and the corresponding address of the port to which the associated slave controller is connected to the master 12.

The addresses of all devices available are initially stored in a memory associated with the VCI such that a multiplexer may be used to activate a specific address or make that address accessible. In this fashion, once the master 12 receives a valid selection command, which it is able to identify, it then routes all the control commands to the VCI of the appropriate slave controller in the case where the device selected is connected to a slave controller. If the selected device is connected directly to the master 12 then the control commands are fed through the decoder 40 of the master 12 and the control information packet is produced and sent to the device via the central processor 44 of the master 12. In this fashion, the VCI of a slave is fed control signals and processes those signals as though they were received from the A/D converter, which is where the input to the slave is routed. Every slave can be attached to one master, and that master, can, in turn be attached to another master, thus providing a daisy-chain of slaves all of which are connected to one master having a microphone attached thereto.

Figure 4:
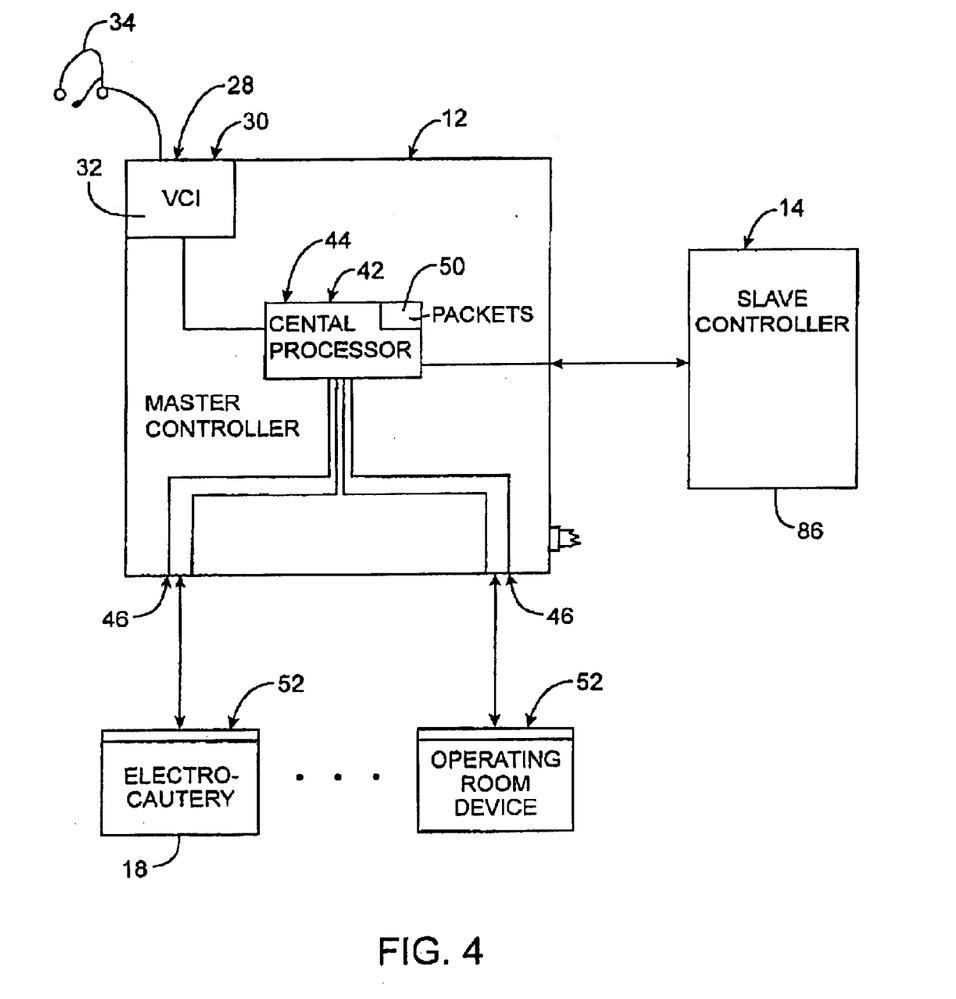
FIG. 4 is an exemplary schematic diagram of a master controller.

In addition to the VCI 32, the master controller 12 comprises means 42 for routing control signals to a device specified by a selection command received at the VCI 32. FIG. 4 depicts the master controller 12 having one slave controller 14 and two medical devices in electrical communication therewith. The master controller includes the VCI 32 as well as the means 42 for routing control signals. Once the speech has been extracted and decoded into either a selection command, or a control command, the specific command is transmitted to the Central Processor 44 of the master controller 12.

In the preferred embodiment, the means 42 for routing control signals is incorporated into the central processor 44 of the master controller 12. The means 42 for routing is essentially an addressable multiplexer and has a memory of the addresses for each device and their associated one of the plurality of communication ports 46 to which they are connected. If the addresses are stored in the decoder 40, then the central processor 44 will be in communication with that memory.

The means 42 for routing, takes the packet 50 of information or the control signal, if the information is to be sent to a slave 14, checks which of the plurality of communication ports 46 it is to direct the information to and then directs the information to the desired one of the plurality 46 of ports.

The addresses and their associated ports are uploaded into the master 12 upon startup of the system. This procedure is embedded in the software and such a procedure is well-known in the art.

For example, in FIG. 4, an electrocautery device 18 transmits an address to the master controller 12. The address is received at a one of a plurality of communication ports 46, the address is saved in the memory along with the associated communication port number. It is to be appreciated that the valid selection commands are stored on the transportable memory. For devices directly connected to the master, the language model may be stored in a memory in the master 12 or in the transportable memory. Language models are stored in associated slaves for devices that are directly connected to a slave 14. In this fashion, upon startup, the master 12 knows all devices that are connected to the system, as each slave sends to the master the addresses of each device and the name (i.e. coded phonemes that constitute the device) of the device. The names of the devices are uploaded into the master so that the validity of selection commands may take place in the master 12. However, language models for the validity of control commands are not transmitted to the master 12 as this would take much time and slow the control system 10 down. Therefore, the master controller 12 actually contains a subset of the grammar necessary to operate the devices in connection therewith, but that language model is limited to only the device names. The information regarding valid sequences of control commands (i.e. their control language model) is stored on each slave controller to which they are connected. Of course, if the device 14 is directly connected to the master, then the language model is stored at the master 12 as described hereinabove.

The control system 10 in accordance with the present invention provides a way to configure and reconfigure an operating room in a very simple fashion. Additionally, it is to be appreciated that the system 10 provides an intuitive interface whereby a user can select a device to control and then subsequently control that device. The system checks to ensure that control commands received for a specific device are valid.

Additionally, the system 10 requires the inclusion of adapters 52 placed intermediate a specific one of the plurality of devices 16 and a slave or the master 12. The adapters 52 transmit signals to their respective slave 14 or master 12 indicative of the address of the device, and translate control signals sent from the controller to which they are connected to signals understood by the particular device for which they are intended. Such adapters are easily constructed and are well-known in the art. Additionally, such adapters may be included either in the respective slave 14 or master 12 or attached to the particular one of the plurality of devices 16 itself. There is substantial advantage to attaching the adapters 52 to the devices 16 as then the devices may be attached to any port, whereas, if the adapters are attached interior the controller 12, 14, the specific device for which they were designed must be attached to the specific one of the plurality of communication ports 46.

If new devices are added to the system, or if improvements or upgrades are made to the system software, such changes may be incorporated into a PCMCIA format card, such as the card that stores the user voice models. The card may be inserted into the same interface, however, system software may be uploaded into the master to make the upgrade without having to disassemble the master. This is accomplished by incorporating a serial interface on the PCMCIA format card. As such, the central processor 44 additionally checks upon startup whether there is a system upgrade to be made by checking the data being supplied by the PCMCIA format card. Checking the activity of a serial interface is well known, however it is not heretofore known to incorporate a serial interface on a single PCMCIA format card. Therefore, the combination is seen to be novel. Additionally, it is heretofore not known to incorporate voice models on such a PCMCIA format card.

In one or more embodiments, each of the at least one slave 14 is substantially similar to the master controller 12. Moreover, each of the plurality of slaves 14 may include the full VCI so that each slave 14 can operate as a master. Alternatively, although not preferred, the slaves may not include the feature extractor, and only contain a subset of the language model (i.e. control commands) relating to the operation of each specific device. This is all that may be necessary in the slave because the slave receives from the master controller the specific address a command is to be sent and that it is in fact a command. Therefore, the slave only needs to check to ensure that it is a valid command for the specific device. In this fashion, devices may be directly connected to the master, or they may be connected to a slave which is in communication with the master 12.

The system 10 may include output means including a video monitor 86 and a speaker 88. The speaker may be incorporated into the VCI 32 via a D/A converter 90 such that the system may communicate to the user any errors committed by the user in operating or selecting a specific device. Additionally, the output means may communicate system errors or the malfunction of a specific device. Such information is included in each specific adapter and is specific to the device attached to the adapter. It is to be appreciated that such communications would be transmitted to the master where they would be either auditorially or visually displayed. The system and controller in accordance with the invention may additionally include a foot controller, a hand controller or other well-known controllers. Each of these controllers may be used to control any of the devices connected to the master or a slave, as is described in the patent application incorporated herein by reference. As such, the VCI may only be used to select certain devices, and once selected the device may be controlled via one of the well-known controllers. Ultimately, the flexibility of such a system can reduce costs and increase the safety of surgical procedures.

The system 10 may include a connection to a hospital computer network via a network gateway 500. Hospital networks are implemented in substantially all hospitals and provide for electrical storage of patient records as well as scheduling and financial information.

The network gateway 500 is preferably a personal computer such as an IBM compatible, or some other well known personal computer running web browsing software such as Microsoft Internet Explorer, Netscape Communicator or any other known web browsing software.

By connecting to the hospital network, patient information that is available at computer terminals in the hospital would also be made available in the operating room. As such, a vocabulary for accessing patient data must be provided to be used with the control system. Examples of such vocabulary include the commands "get", "load" and "display". The data that may be provided includes, but is not limited to x-rays, patient history, MRIs, angiography and CAT scans.

Through the use of a web browser, the patient data may be sent to the gateway 500 in a format to be displayed by either a monitor 510 connected to the gateway or directly to the monitor. This would be accomplished through electrical connections already disclosed hereinabove.

To effectuate the display of patient data in a web browsable format, essentially HTML or some other well known web format, the data must be provided to the gateway 500 in such. An access port, essentially consisting of a URL provides a location for the web browser to obtain patient information. This URL provides an interface into the hospital network.

Figure 6:
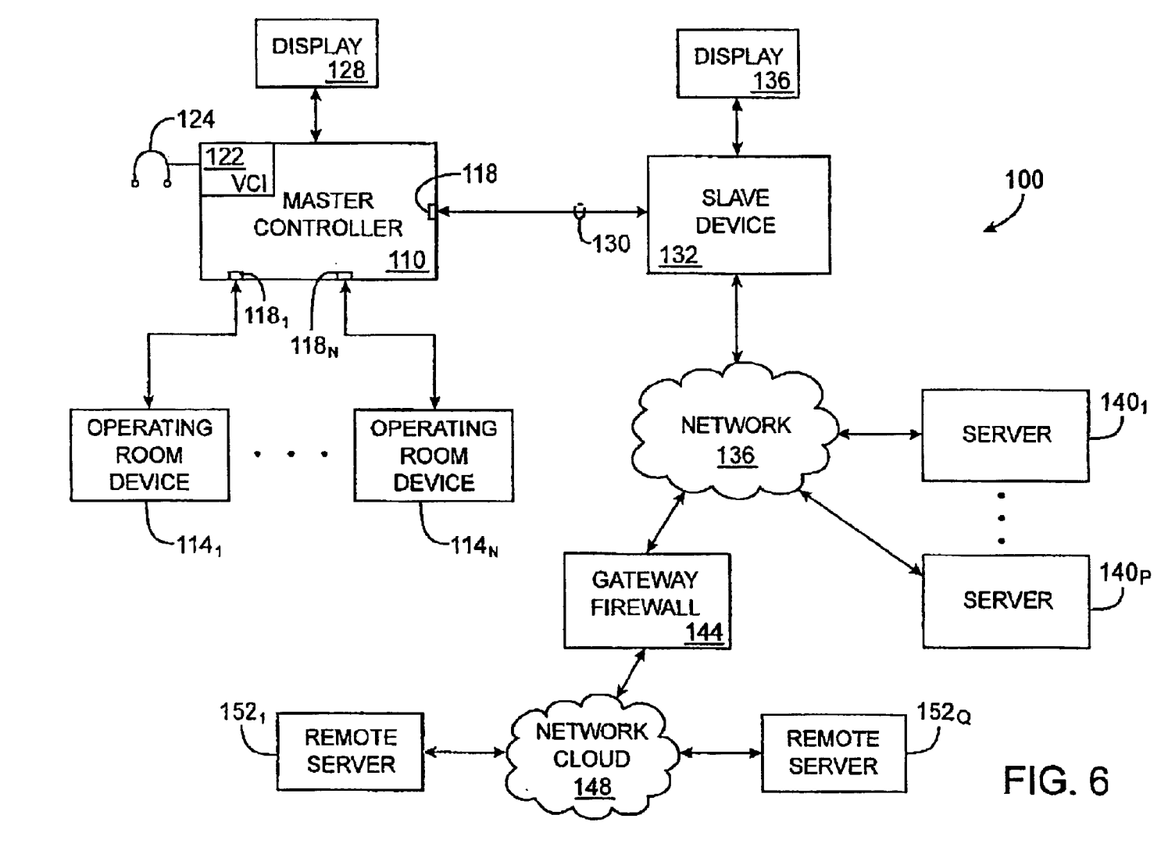
FIG. 6 illustrates a block diagram of a control system, according to another embodiment of the present invention.

FIG. 6 illustrates a block diagram of a control system 100, according to another embodiment of the present invention. The control system 100 may be accessed and utilized in an operating room, a doctor's office, or other location, e.g., where surgery, medical attention, or examination is provided. For sake of illustration, the control system 100 will be described with respect to an operating room setting, and thus will be referred to as an operation room control system. The control system 100 allows an operator (e.g., a surgeon, nurse, technician, etc.) to control operating room devices, retrieve, view, and manipulate patient records and information, and store information regarding the patient (e.g., notes, X-rays, pictures, etc.) before, during, or after the surgery, examination, etc., conduct video conferencing and remote surgery, and the like.

Referring to FIG. 6, the operating room control system 100 includes a master controller 110 that is coupled to a plurality of operating room devices $114_1$–$114_N$ via respective communication ports $118_1$–$118_N$, where "N" is a positive whole number. The communication ports $118_1$–$118_N$ may include any type communication port such as a serial port, parallel port, high speed serial bus, etc., and combinations thereof. The operating room devices $114_1$–$114_N$ may include any operating room device as mentioned hereinabove such as a robotic arm, electrocautery device, operating room table, operating room lights, insufflator, camera, and the like.

The master controller 110 is coupled to a display device 128 for displaying information (e.g., status of operating room devices, video captured by an endoscope, etc.) to the surgeon, doctor, nurse, etc. The master controller 110 also includes a VCI 122 for receiving selection and control commands, as described above and shown in FIG. 2, from an input device such as a microphone/headset 124. In one embodiment, the master controller 110 includes a processor (e.g., microprocessor), memory (random access and non-volatile), communication circuitry, etc. The operating system may execute a speech recognition program for receiving audible commands to perform various tasks as discussed herein.

The master controller 110 is also coupled to a slave device 132 via communication port 118 and communication lines 130. In one embodiment, the slave device 132 is a device that performs actions and tasks requested by the master controller 110, and includes a processor (e.g., microprocessor), memory, display card, communication card (e.g., network interface card), and other components well known to those skilled in the art, none of which are shown. The slave device 132 is coupled to a display 136 for displaying patient information, images, files, and the like, as will be discussed below. The slave device 132 may simply act as another "operating room device", with the purpose of retrieving, storing, and displaying patient information as requested by the master controller 110. The master controller 110 may be coupled to the slave device 132 via serial port, parallel port, network connection, modem, high speed serial bus, radio frequency connection, and infrared connection.

It is important to note that the function of the slave device 132 as herein described may be performed partially or entirely by the master controller 110. In such a case, the patient information would be retrieved directly from the network 136 and displayed on the display 128.

The slave device 132 executes an operating system such as Windows™ or Linux™, and executes one or more application programs, modules, and/or drivers for communicating with the master controller 110, retrieving, displaying, and storing patient information, images, etc. on the display 136. In one embodiment, the slave device runs a web browser program such as the Internet Explorer™, Netscape Navigator™, etc. for accessing medical records over a network (e.g., Internet, Intranet, etc.).

The slave device 132 is coupled to a network 136, which may be a local area network (LAN), a wide area network (WAN), etc., and a combination thereof. The protocol used by the network may include TCP/IP or other suitable protocol. Coupled to the network 136 are, among other things, servers $140_1$–$140_P$, where "P" is a positive whole number. The servers $140_1$–$140_P$ may be one or more dedicated servers, department computers, and combinations thereof. The one or more severs and/or computers may each include databases containing patient information including, among other things, MR, CT, X-ray, still-frame video, moving video, ultrasound images, patient records, scheduling, financial information, and inventory (e.g., equipment usage). The data may be captured by a surgeon, doctor, nurse, technician, e.g., during Radiology, Pathology, surgery, examination, etc. For example, one of the servers may be dedicated for storing X-rays of patients, another dedicated for storing patient records, and the like. The servers $140_1$–$140_P$ may be physically located within the hospital, medical center, etc. Additionally, one or more of the servers $140_1$–$140_P$ may be located at different locations of a health organization, affiliates, etc., but accessible via a closed network such as network 136.

By connecting the slave device 132 to the network 136, patient information is available for retrieval by the master controller 110 at any time including during surgery, examination, etc.

The master controller 110 also includes a language model (or vocabulary) for audibly accessing patient information from various sources through the slave controller 132. Examples of such audible commands available include, but are not limited or restricted to "get", "load", "display", "rotate", "store", etc. Natural language voice commands may also be used to identify which patient records to retrieve and view, to enlarge or shrink images, to adjust brightness and contrast, to page forward to the next image or back to the previous image, etc. A surgeon may capture and store images or video, record and store audio, or store text audibly at any time including during surgery or examination. The stored information can then be "uploaded" as part of the patient information in the one or more servers $140_1$–$140_P$. The master controller 110 and/or slave device 132 may include software and/or hardware for distinguishing the type of information stored (e.g., X-ray, patient information, etc.) and uploading the different types of information to different servers.

The slave device 132 is also coupled to a gateway/firewall 144 for communicating over network cloud 148 such as the Internet or other network. The gateway/firewall 144 includes a controller (not shown) that controls traffic within the network 136 and provides access to the outside network cloud 148. The gateway/firewall 144 may also perform translation from one protocol to another, routing functions, etc. Also coupled to the network cloud 148 are one or more remote servers $152_1$–$152_Q$ (where "Q" is a positive whole number). The remote servers $152_1$–$152_Q$ may be located at one or more remote hospitals, health organizations, and/or dedicated locations (e.g., central databases). Consequently, a doctor can obtain patient information (e.g., picture of a patient's heart valve) from a hospital that the patient previously visited, while performing emergency heart valve surgery on the patient. The slave device 132, under command of the master controller 110, can retrieve patient information from and store patient information to one or more remote servers $152_1$–$152_Q$.

Through the use of a web browser, the patient information may be sent to the slave device 132 in a format to be displayed by either the display 136 or the display 128 connected to the master controller 110, in a web browsable format.

To effectuate the display of patient information in a web browsable format, using HyperText Markup Language (HTML) or some other well known web format, the data is provided to the slave device 132 in that format. An access port, essentially consisting of one or more URLs provides a location for the web browser to obtain patient information. The one or more URLs provide an interface into the network 136 and network cloud 148. The web browser can display an index of medical records, images, etc., with voice-activated links to more detailed information.

Figure 7:
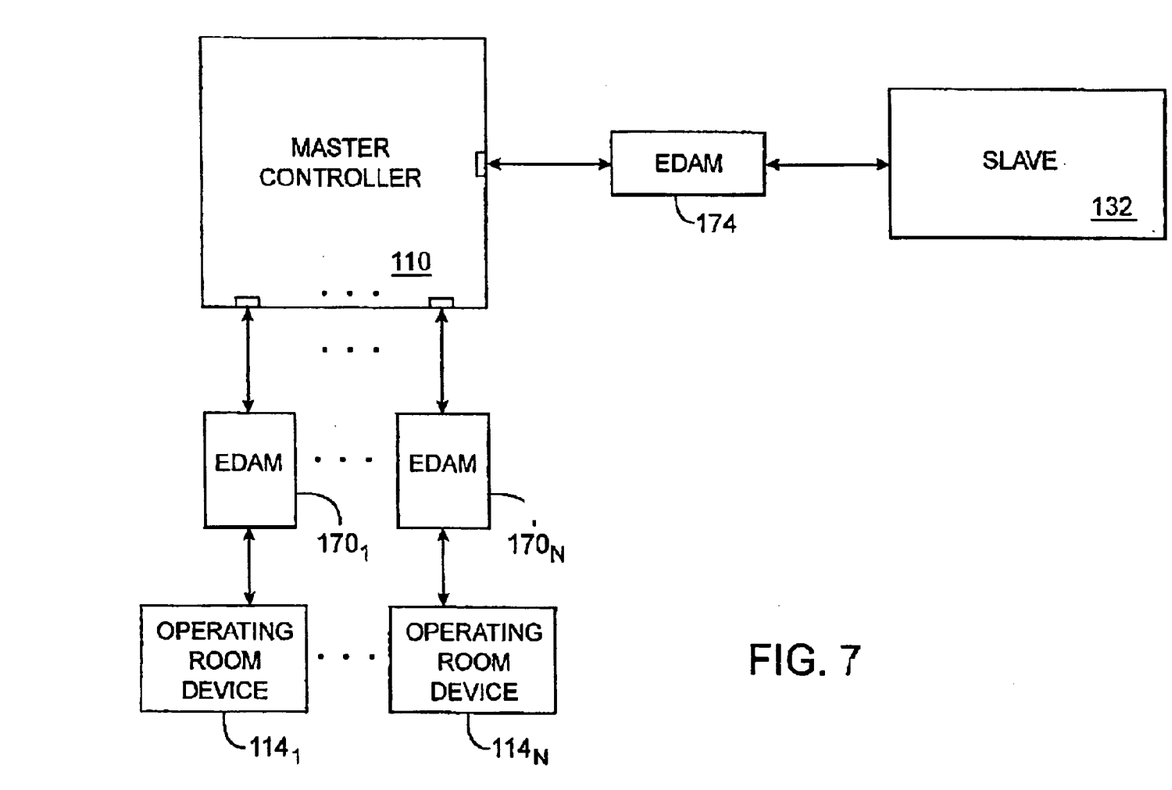
FIG. 7 shows a logical connection between the master controller and the operating room devices including the slave device.

FIG. 7 shows a logical connection between the master controller 110 and the operating room devices $114_1$–$114_N$ and the slave device 132. Referring to FIG. 7, the master controller 110 is coupled to the operating room devices $114_1$–$114_N$ via respective modules $170_1$–$170_N$, and is coupled to the slave device 132 via module 174. The modules are software blocks or drivers that translate signals and/or commands between the master controller 110 and the operating room devices $114_1$–$114_N$, and the slave device 132. In one embodiment, a module is a dongle that translates signals from the master controller 110 to a specific format (e.g., protocol, timing, etc.) of the particular operating room device or slave device, and vice versa. Thus, the modules may be different depending on the device being controlled. Each of the modules $114_1$–$114_N$ continuously "pings" or monitors the device being controlled to confirm that device is operational. This allows the master controller 110 to quickly determine whether a device has malfunctioned and provide prompt notification, which may be critical in the operating room environment. In another embodiment, the modules $114_1$–$114_N$ may be hardware devices or combination of hardware/software devices, where the hardware devices include circuitry for performing translation of signals, timing, and the like.

Figure 8:
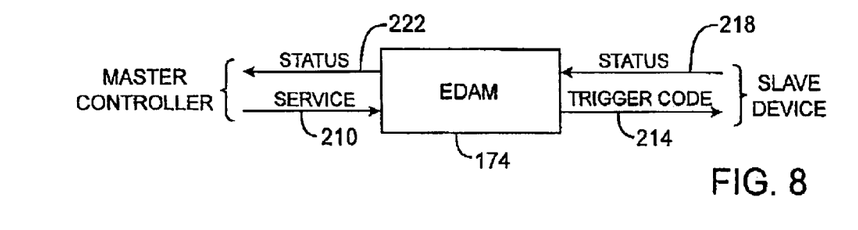
FIG. 8 shows a logical connection of the module that interfaces the master controller to the slave device.

FIG. 8 shows a logical connection of the module 174 that interfaces the master controller 110 to the slave device 132. The master controller 110 issues service requests or commands 210. If a voice command received by the master controller 110 is a recognized command for querying the slave device 132 for information, the master controller 110 forwards a service request 210 (e.g., "get angiography information") to the module 174. The module 174 translates and/or processes the command into a format recognized by the slave device and forwards a trigger code command 214 to the slave device 132. The slave device 132 receives the command for processing. The slave device 132 then sends status commands 218 back to the module 174, indicating the status of the request, retrieved information, etc. The module 174, in turn, transmits the status command 222 to the master controller 110, indicating the status. For example, if the angiography information of a patient is not available, then the status will indicate this information. The slave device 132 may also deactivate any portion of the display 126 (FIG. 6) pertaining to the angiography information to indicate that the information is not available. The master controller 110 continually sends commands (e.g., in short intervals) to the slave device 132 for obtaining the operational status of the slave device 132.

Figure 9:
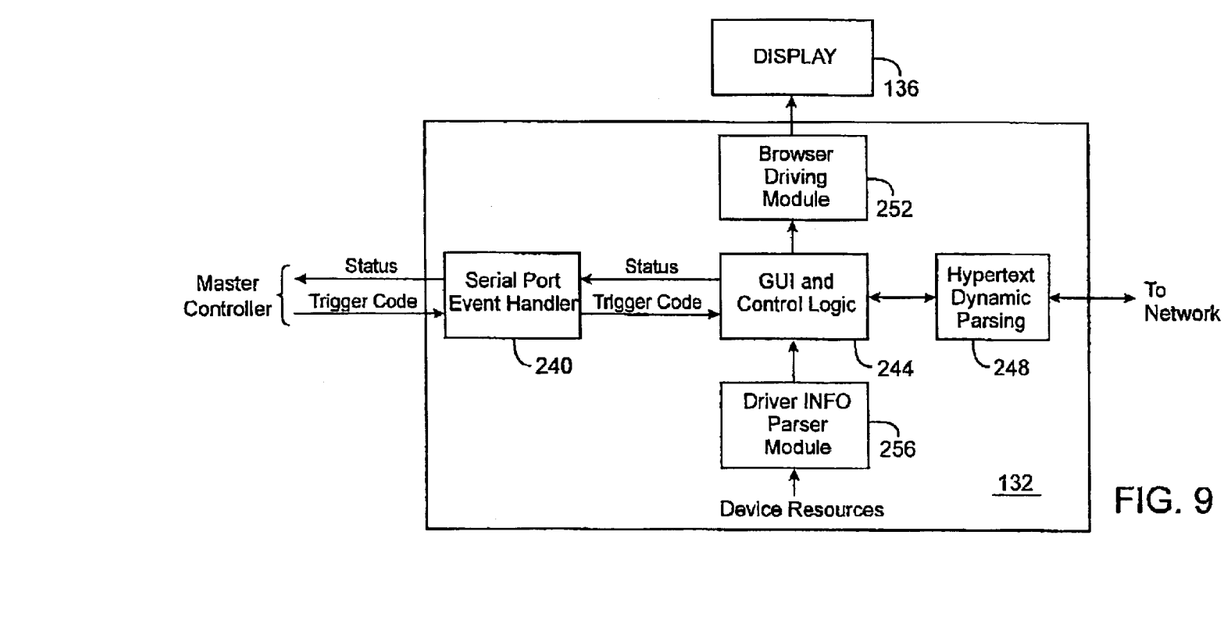
FIG. 9 illustrates a logical block diagram of the slave device, according to one embodiment of the present invention.

FIG. 9 illustrates a logical block diagram of the slave device 132, according to one embodiment of the present invention. Referring to FIG. 9, the slave device 132 includes a serial port event handler 240 that receives trigger codes from and sends status information to the module 174 (FIG. 8). The event handler 240 forwards the received trigger codes to a graphical user interface (GUI) and control logic block 244. The GUI and control logic block 244 sends commands to a hypertext dynamic parsing module 248, which then transmits the request to one or more servers, located on the network 136 (e.g., Intranet) and/or on the network cloud 148 (e.g., Internet). In one embodiment, the information transmitted from servers to the slave device 132 is in hypertext format. The hypertext dynamic parsing module 248 receives the hypertext data from one or more servers, parses the data for images, text (e.g., patient records), video clips, dynamic links, etc., and forwards the parsed information to the GUI and control logic block 244. The GUI and control logic block 244 drives the information to a browser driving module 252 for displaying the information on the display 136.

Also coupled to the GUI and control logic block 244 is a driver information parser module 256, which provides configuration information to the GUI and control logic block 244. The module 256 is loaded once during initialization. It retrieves information from a configuration or device resource file, and forwards the information to the GUI and control logic block 244. The configuration information indicates resources available, such as, for example, the voice commands available, the menu structure to be displayed on the display 136, timing requirements, and the like.

The GUI and control logic block 244 receives the trigger code, translates the code based on the current patient, and forwards a command to a server (e.g., patient #2100, angiography). The server receives the command, retrieves the angiography information for patient #2100, if any, from its database, and sends the information back. The parsing module parses the information.

Figure 10:
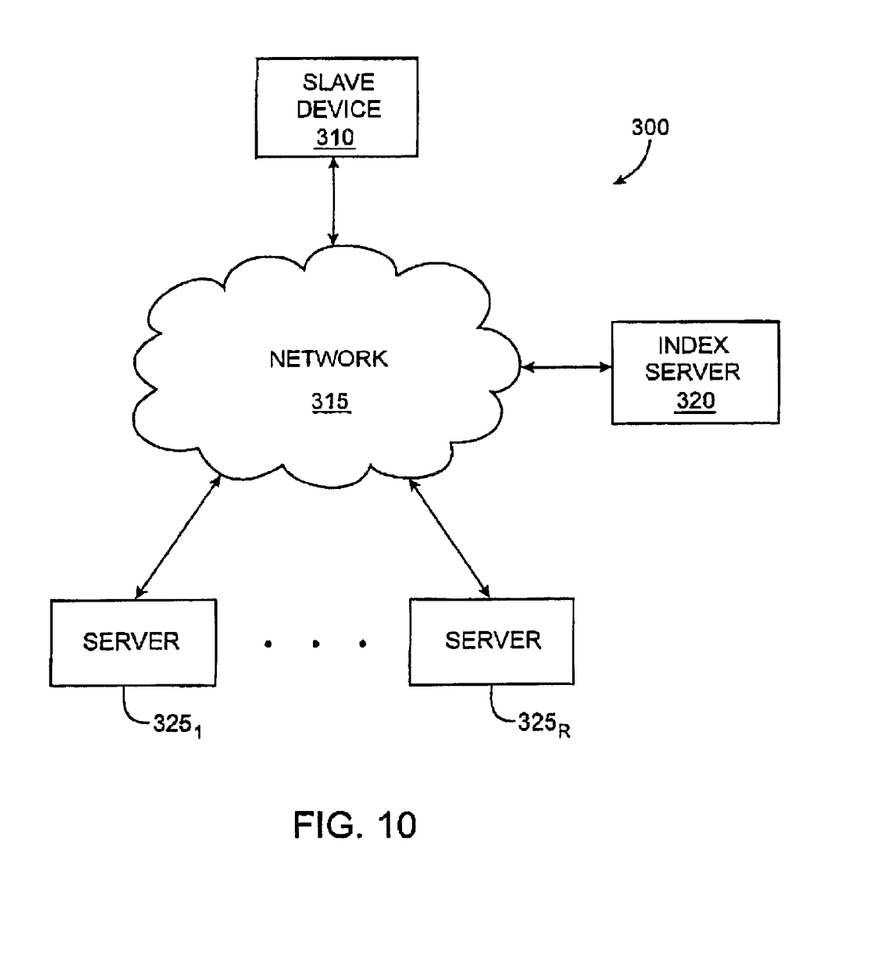
FIG. 10 illustrates a block diagram of a system, according to another embodiment of the present invention.

FIG. 10 illustrates a block diagram of a system 300, according to another embodiment of the present invention. Referring to FIG. 10, the system 300 includes a slave device 310, which comprises the slave device 132 of FIG. 6. Other devices such as the master controller 110, operating room devices $114_1$–$114_N$, display devices 128 and 136, and microphone/headset 124 have not been shown for sake of clarity. In an embodiment where the master controller 110 performs the functions of the slave device 132, the slave device 310 comprises the master controller 110 (FIG. 6). The system 300 is developed for accessing disparate medical data across a network 315, which represents a local area network, wide area network, direct connection, or combinations thereof.

The system 300 includes an index server 320 that is coupled to the network 315. The index server 320 accepts queries from the slave device 310 for medical data about a specific patient and provides a reference list of records available about that specific patient. The slave device 310 and the index server 320 may be located within the same hospital, group of hospitals, or remotely from each other. The medical data are derived from a discrete set of electronic medical record servers $325_1$–$325_R$ (where "R" is a positive whole number). The servers $325_1$–$325_R$ may be located remotely from each other. For example, the servers $325_1$–$325_R$ may represent servers located domestically and/or globally of one or more of the following: hospitals, medical centers, centralized medical data databases, and the like.

The medical data referenced may be of any variety including photographic (still or moving), textual, aural, or other patient data. In one embodiment, the index server 320 receives requests from the slave device 310 and responds with an HTML protocol that reflects the results of the patient data located. Further, the index server 320 may format certain datas in an HTML protocol to facilitate display of such data by the slave device 310.

The present invention may be implemented as a method, apparatus, system, etc. When implemented in software, the elements of the present invention are essentially the code segments to perform the necessary tasks. The program or code segments can be stored in a processor readable medium or transmitted by a computer data signal embodied in a carrier wave over a transmission medium or communication link. The "processor readable medium" may include any medium that can store or transfer information. Examples of the processor readable medium include an electronic circuit, a semiconductor memory device, a ROM, a flash memory, an erasable ROM (EROM), a floppy diskette, a CD-ROM, an optical disk, a hard disk, a fiber optic medium, a radio frequency (RF) link, etc. The computer data signal may include any signal that can propagate over a transmission medium such as electronic network channels, optical fibers, air, electromagnetic, RF links, etc.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. An operating room control system for use during a medical procedure on a patient, comprising:
   a plurality of operating room devices;
   a voice input device capable of receiving a spoken device command that has an associated device qualifier, and a data retrieval command having an associated patient record identifier;
   a display device; and
   a controller coupled to the input device and the display device, the controller capable of receiving the data retrieval command and the device command, wherein the controller transmits a command to a server to retrieve patient information in response to the data retrieval command so that desired patient data can be selected in response to the patient record identifier, wherein the controller receives the patient information from the server and displays the patient information on the display device, and wherein the controller transmits a control command to a selected operating room device in response to the device command, the medical operating room device selected from the plurality of operating room devices in response to the device qualifier so as to allow voice manipulation of an operating room environment.

2. The operating room control system of claim 1 wherein the server is located outside the operating room.

3. The operating room control system of claim 1 wherein the patient information includes one or more of the following: an MRI, CT, X-ray, still-frame video, moving video, ultrasound image, patient records, patient notes, and patient schedule.

4. The operating room control system of claim 1 wherein the server is coupled to the controller via one or more of the following: a local area network, wide area network, Internet, and Intranet.

5. The operating room control system of claim 1 wherein the controller includes a memory containing an application program, and a processor, said processor to execute the application program to cause the patient information to be displayed on the display device in a web browseable format.

6. The operating room control system of claim 1 wherein the input device comprises one or more of the following: a microphone, keyboard, mouse, foot pedal, and hand-held device.

7. The operating room control system of claim 1, wherein the controller compares the device command with a list of stored control commands associated with the selected operating room device, and transmits a control signal to a medical instrument for controlling the operating room device if there is a match, wherein the operating room devices comprise one or more of the following: a robotic arm, electrocautery device, operating room table, operating room lights, insufflator, and camera.

8. The operating room control system of claim 1 wherein the controller captures one or more units of patient data, transmits the one or more units of data and a request to a second server located outside the operating room to store the one or more units of patient data.

9. The operating room control system of claim 8 wherein the second server is coupled to the controller via one or more of the following: a local area network, wide area network, Internet, and Intranet.

10. The operating room control system of claim 8 wherein the one or more units of patient data comprises one or more of the following: an image captured by an image capturing device coupled to the controller, a moving video captured by the image capturing device coupled to the controller, and notes captured via the input device regarding the patient.

11. A method for accessing medical data from a server while performing a medical procedure, comprising:
   receiving a plurality of commands from an input device including an instrument command that has an associated instrument qualifier, and a data retrieval command having an associated patient record identifier;
   transmitting a request to the server for the unit of patient data in response to the data retrieval command;
   receiving the unit of patient data from the server; and
   displaying the unit of patient data on a display device.

12. The method of claim 11 wherein the server is located remotely from a location where the medical procedure is performed.

13. The method of claim 11 wherein the instrument command, associated instrument qualifier, data retrieval command and associated data retrieval qualifier each comprise an audible command.

14. The method of claim 11 wherein transmitting the request to the server comprises transmitting a URL of the server for the unit of patient data.

15. The method of claim 11 wherein the unit of patient data includes one or more of the following: an MRI, CT, X-ray, still-frame video, moving video, ultrasound image, patient records, patient notes, and patient schedule.

16. The method of claim 11 further comprising:
   capturing a second unit of patient data during the medical procedure;
   transmitting the second unit of patient data to a second server with a request to store the second unit of patient data.

17. The method of claim 11, further comprising transmitting a control signal to one or more medical instruments in response to the instrument command.

18. The method of claim 17, wherein transmitting a control signal comprises comparing the instrument command with a list of one or more stored control commands associated with the one or more medical instruments, and transmits one or more control signals to a medical instrument for controlling the medical instrument if there is a match.

19. The method of claim 18, wherein the medical instruments comprise one or more of the following: a robotic arm, electrocautery device, insufflator, and camera.

20. An operating room control system for use during a medical procedure on a patient, comprising:

- a plurality of medical devices, each device having an associated device identifier;
- a voice input device capable of receiving spoken device commands having associated device qualifiers, and also capable of receiving spoken voice data retrieval commands having an associated data retrieval qualifier;
- a display device;
- a master controller coupled to the input device, the master controller capable of receiving the data retrieval commands and the device commands, wherein the master controller receives a command having a qualifier and transmits the command to a network so as to retrieve a unit of information when the qualifier is a data retrieval qualifier, and wherein the master controller transmits the command to a selected medical device when the qualifier is a device qualifier, the selected medical device being selected from the plurality of medical devices and having an associated device identifier matching the device qualifier; and
- a slave controller coupled to the master controller and the display device, the slave controller capable of transmitting a request for the unit of information to a server, receiving the unit of information from the server, and displaying the unit of information on the display device.

21. The operating room control system of claim 20 wherein the unit of information includes one or more of the following: an MRI, CT, X-ray, still-frame video, moving video, ultrasound image, patient records, patient notes, and patient schedule.

22. The operating room control system of claim 20 wherein the server is coupled to a slave controller via one or more of the following: a local area network, wide area network, Internet, and Intranet.

23. The operating room control system of claim 20 wherein the request for the unit of information includes a patient identification number.

24. The operating room control system of claim 20 wherein the server is located remotely from the slave controller.

* * * * *